US008821787B2

(12) United States Patent
Marenco et al.

(10) Patent No.: US 8,821,787 B2
(45) Date of Patent: Sep. 2, 2014

(54) CATALYTIC COMPOSITION HAVING A CORROSION-INHIBITING EFFECT, METHOD FOR INHIBITING CORROSION AND USE OF SAME

(75) Inventors: Carlos Eduardo Marenco, São Paulo (BR); Wagner Lourenco, São Paulo (BR); Renato Bresciani, São Paulo (BR); Sergio Martins, São Paulo (BR); Mario Pattaro, São Paulo (BR); Wellington Bonifacio, Barão Geraldo (BR); João Carlos Lazarini, São Paulo (BR)

(73) Assignee: Rhodia Poliamide e Especialidades Ltda, Sao Paulo (BR)

( * ) Notice: Subject to any disclaimer, the term of this patent is extended or adjusted under 35 U.S.C. 154(b) by 0 days.

(21) Appl. No.: 13/701,800

(22) PCT Filed: May 19, 2011

(86) PCT No.: PCT/IB2011/001078
§ 371 (c)(1),
(2), (4) Date: Jan. 3, 2013

(87) PCT Pub. No.: WO2011/151691
PCT Pub. Date: Dec. 8, 2011

(65) Prior Publication Data
US 2013/0112107 A1    May 9, 2013

(30) Foreign Application Priority Data
Jun. 3, 2010 (FR) ...................................... 10 54364

(51) Int. Cl.
*B08B 17/00* (2006.01)
*C23F 11/00* (2006.01)
*B08B 7/00* (2006.01)
*B08B 9/00* (2006.01)
*B08B 9/20* (2006.01)
*C02F 1/00* (2006.01)
*A61L 9/05* (2006.01)
*C02F 5/00* (2006.01)

(52) U.S. Cl.
CPC ... *C02F 1/00* (2013.01); *A61L 9/05* (2013.01); *C02F 5/00* (2013.01); *C23F 11/00* (2013.01)
USPC ....... 422/7; 422/6; 134/6; 134/22.1; 134/25.1

(58) Field of Classification Search
CPC ............... A61L 9/05; C02F 1/00; C02F 5/00; C23F 11/00
USPC ............. 422/6–7, 187, 256, 292; 134/6, 22.1, 134/25.1
See application file for complete search history.

(56) References Cited

U.S. PATENT DOCUMENTS

| 4,365,081 A * | 12/1982 | Shimizu et al. ............... 560/209 |
| 2009/0012324 A1 | 1/2009 | Choi et al. | |

FOREIGN PATENT DOCUMENTS

| EP | 0 066 059 A1 | 12/1982 | |
| EP | 0 158 499 A2 | 10/1985 | |
| EP | 1 220 829 B1 | 7/2002 | |
| EP | 1 253 113 A1 | 10/2002 | |
| EP | 2 060 555 A1 * | 5/2009 | ............. C07C 51/12 |
| WO | 2007/099071 A1 | 9/2007 | |

OTHER PUBLICATIONS

International Search Report issued on Oct. 14, 2011, by the European Patent Office as the International Searching Authority in Internation Patent Application No. PCT/IB2011/001078.

* cited by examiner

*Primary Examiner* — Monzer R Chorbaji
(74) *Attorney, Agent, or Firm* — Dentons US LLP

(57) ABSTRACT

A catalytic composition with a corrosion-inhibiting effect on metal surfaces is described. Also described, is a corrosion-inhibiting process and use of a corrosion inhibitor. Further, the catalytic composition can have a corrosion-inhibiting effect on metal surfaces in contact with an esterification medium comprising a carboxylic acid and an alcohol, wherein the composition comprises as a catalyst, a strong protonic acid and, as corrosion inhibitor, an iron(III) carboxylate.

20 Claims, No Drawings

CATALYTIC COMPOSITION HAVING A CORROSION-INHIBITING EFFECT, METHOD FOR INHIBITING CORROSION AND USE OF SAME

CROSS-REFERENCE TO PRIOR APPLICATIONS

This application is a National Stage of PCT/IB2011/001078, filed May 19, 2011, and designating the United States (published in English on Dec. 8, 2011, as WO 2011/151691 A1; the title and abstract were published in English), which claims priority to French Patent Application No. 10/54364, filed Jun. 3, 2010, each hereby expressly incorporated by reference in its entirety and each assigned to the assignee hereof.

The present invention relates to a catalytic composition with a corrosion-inhibiting effect on metal surfaces in contact with an esterification reaction medium comprising a carboxylic acid, an alcohol and an acid catalyst.

The invention is also directed toward a process for inhibiting the corrosion of such metal surfaces, and also to the use of a specific compound as a corrosion inhibitor in an esterification reaction between a carboxylic acid and an alcohol, in the presence of an acid catalyst.

Esterification processes, and especially those for the manufacture of ethyl acetate, must be as efficient as possible, in terms of productivity, and lead to a quality product.

Specifically, as ethyl acetate is a common large-volume consumer product, manufactured in industrial installations, the economic factors relating to its production have a significant impact.

The standard processes for manufacturing ethyl acetate use acid catalysts, often sulfuric acid when it is a matter of performing an esterification step coupled to a distillation step, as described, for example, in patent GB 1 173 089. They may also be sulfonic resins when these processes use a reactive distillation as described in patent application EP 1 220 829.

However, the presence of acetic acid, of the acid catalyst and of impurities formed during the reaction (for instance sulfate salts) in such processes functioning at relatively high temperatures (about 100° C. and higher) is the cause of substantial corrosion phenomena.

These phenomena are reflected by degradation and fouling of the walls of the equipment in contact with these acids. The term "fouling" means that salts, in particular iron, nickel and chromium salts, derived from the corrosion process are deposited on the walls. This especially concerns the walls of the reactor, of the reactive distillation column, of the reboilers, and of the pipes, pumps and valves. For the walls of equipment such as the reboiler, these phenomena lead to a reduction in the area for exchange and in the overall heat transfer coefficient of the reboiler. Such phenomena thus necessitate frequent production stoppages for maintenance of the equipment. This especially involves replacing or treating the corroded or fouled surfaces. These frequent interruptions in the manufacture of ethyl acetate represent losses in terms of productivity, of production capacity of the installation and of equipment cost for the manufacturers. Specifically, firstly, the fouling of the walls of the reboilers leads to a reduction in the productivity of ethyl acetate since the exchange coefficient between the vapor heating the reactor and the reaction medium is decreased. Secondly, the frequent stoppages represent times during which the unit is not producing ethyl acetate.

It is known practice to use reactors made of materials that are reputed to be stainless, but such equipment is expensive or is insufficiently resistant to corrosion by acetic acid and the acid catalyst.

It is also known practice to use corrosion inhibitors to reduce corrosion phenomena. This may especially be a case of using oxidative metal cations such as copper or iron in the form of sulfates, especially in media comprising oxidative acids such as sulfuric acid. This being the case, such compounds are not efficient enough to prevent the corrosion of equipment in media comprising acetic acid and an acid catalyst, especially at temperatures above 100° C., and the corrosion phenomena are still observed.

The object of the present invention is thus to overcome the abovementioned drawbacks associated with the corrosion of installations by the carboxylic acids and acid catalysts used during an esterification reaction between a carboxylic acid and an alcohol, in the presence of an acid catalyst.

With this aim, the present invention provides a composition, especially a catalytic composition with a corrosion-inhibiting effect on the metal surfaces in contact with an esterification medium comprising a carboxylic acid and an alcohol, characterized in that it comprises at least, as catalyst, a strong protonic acid and, as corrosion inhibitor, an iron(III) carboxylate.

Another subject of the invention is a process for inhibiting the corrosion of the metal surfaces in contact with an esterification medium comprising a carboxylic acid, an alcohol and a strong protonic acid as catalyst, characterized in that an iron(III) carboxylate, preferably corresponding to the carboxylic acid to be esterified, is used in an esterification reaction between said carboxylic acid and said alcohol in the presence of said strong protonic acid.

Another subject of the invention is the use of an iron(III) carboxylate as a corrosion inhibitor for the metal surfaces in contact with an esterification medium comprising a carboxylic acid, an alcohol and a strong protonic acid catalyst.

The composition, the process and the use according to the present invention specifically make it possible to considerably limit the phenomena of corrosion and fouling by the carboxylic acids and acid catalysts used during the esterification reaction and thus to avoid the production stoppages for replacement or cleaning of the fouled surfaces. Thus, the present invention enables a gain in productivity due to the maintenance of a good coefficient of exchange between the vapor and the medium that is to be heated over time, an economic gain relating to the longer surface life of the equipment, and also a maximum production capacity of the installation which no longer requires corrosion-related production stoppages. The term "corrosion inhibition" means that the rate of corrosion must be less than 0.125 mm/year, preferably less than 0.05 mm/year and even more preferentially less than 0.01 mm/year.

The particular embodiments of the invention described below apply to the composition, to the process and also to the use according to the invention.

In accordance with one embodiment of the invention, the iron(III) carboxylate is that corresponding to the carboxylic acid to be esterified, preferably iron(III) acetate. The iron(III) carboxylate is advantageously a compound that is soluble in the esterification medium.

The carboxylic acid to be esterified is advantageously chosen from aliphatic carboxylic acids containing from 1 to 6 carbon atoms; it is preferably acetic acid.

The carboxylic acid to be esterified is advantageously introduced pure or in highly concentrated aqueous solution. The invention does not exclude the presence of water in the carboxylic acid. However, it is preferable to use the carboxylic acid neat due to the subsequent need to remove the water present in the carboxylic acid ester obtained.

The alcohol involved is preferably an alcohol comprising a linear or branched alkyl chain having from 1 to 6 carbon atoms or an alcohol comprising a cycloalkyl chain having 5 or 6 carbon atoms.

Preference is given in particular to alcohols comprising a low boiling point, in particular of less than 170° C., preferably of less than 165° C.

Thus, the alkyl-chain alcohol is advantageously chosen from ethanol, n-propanol and butanol, preferably ethanol.

The alcohol comprising a cycloalkyl chain is preferably cyclohexanol.

An excess of one of the reagents may be advantageous to shift the reaction equilibrium toward the production of carboxylic acid ester.

Thus, the mole ratio between the carboxylic acid and the alcohol may be between 0.9 and 25 and preferably between 1 and 20.

An excess of carboxylic acid relative to the alcohol is generally preferred, preferably with a mole ratio between the carboxylic acid and the alcohol of between 7 and 25 and especially between 9 and 20.

The upper limit, for economic reasons, is advantageously chosen to be less than 25. The ratio precisely defined corresponds to the mole ratio of the reagents at the start of the reaction.

The catalyst involved in the invention is a strong protonic acid catalyst. It may be an acid catalyst that is liquid (or soluble in the reaction medium) enabling homogeneous catalysis or an acid catalyst that is solid (insoluble in the reaction medium) enabling heterogeneous catalysis.

According to a first mode, the catalyst is a liquid acid catalyst enabling homogeneous catalysis.

In the present invention, the term "strong protonic acid" denotes an acid with a pKa in water of less than 2 and preferably less than 1.

The pKa is defined as follows: pKa=−log Ka, Ka being the ionic dissociation constant of the acid/base pair at room temperature (generally 25° C.), when water is used as solvent.

Among the acids corresponding to this definition, it is preferable to use an acid which does not result in side reactions harmful to the esterification process and which in particular does not have an oxidative nature, such as nitric acid.

Sulfuric acid, sulfonic acids and mixtures thereof may be mentioned more particularly as strong protonic acid.

Mention may in particular be made, as sulfonic acids, of fluorosulfonic acid, chlorosulfonic acid or trifluoromethanesulfonic acid, methanesulfonic acid, ethanesulfonic acid, camphenesulfonic acid, benzenesulfonic acid, toluenesulfonic acids, xylenesulfonic acids or naphthalenesulfonic acids.

Among these acids, the preferred catalyst is chosen from para-toluenesulfonic acid and methanesulfonic acid, preferably methanesulfonic acid.

According to a second mode, the catalyst is a solid acid catalyst leading to heterogeneous catalysis.

The solid acid catalysts of the invention are preferentially sulfonic resins or zeolites.

The zeolites which can be used are, for example, those cited in the document WO 2007/099 071.

The resins that are suitable for use in the present invention may consist of a polystyrene or polyacrylic backbone bearing sulfonic or carboxylic functional groups.

Thus, use may be made of commercial sulfonic acid $SO_3H$ or carboxylic acid COOH resins, which resins are sold under various trade names.

Mention may be made, inter alia, of the following esterification resins: Amberlyst® 15 from Rohm & Haas, Amberlite® IR-120H from Rohm & Haas, and Lewatit® 2631 and K1431 from Bayer.

The acidity of these resins is, for example, between 1 and 10 eq/kg (H+).

These resins are used in particular in a fixed or fluidized bed, preferably in a fixed bed.

The amount of strong protonic acid catalyst introduced is preferably between 0.05% and 15% by mass, preferably from 0.1% to 10% by mass and especially from 0.2% to 2% by mass relative to the mass of reaction medium at the start of the reaction.

According to the invention, the esterification reaction is preferably performed under conditions such that the reaction mixture is in liquid form.

According to a first embodiment of the invention, the esterification reaction is performed in a two-step process: an esterification reaction followed by a distillation operation. The esterification reaction may be performed under homogeneous or heterogeneous catalysis, preferably under homogeneous catalysis.

The esterification reaction is preferably performed in an esterification reactor.

In accordance with the invention, the esterification reaction may be performed in continuous or batch mode, preferably in continuous mode.

In the esterification reactor, the carboxylic acid and the alcohol may be introduced alone or as a mixture, preferably as a mixture.

According to one embodiment of the invention, the esterification reaction is performed at a temperature of at least 50° C.

Advantageously, the reaction temperature is between 50 and 150° C., preferably between 100 and 130° C.

According to the invention, the esterification reaction is preferably performed at a pressure such that the reaction mixture is in liquid form.

The reaction is preferably performed at atmospheric pressure. A pressure slightly higher or lower than atmospheric pressure may also be suitable for use. Thus, the esterification reaction may be performed, for example, at an absolute pressure of between 0.5 and 5 bar absolute.

The reaction mixture thus obtained after the esterification reaction is then subjected to a distillation operation in order to obtain at the distillation head a vapor stream comprising in major amount the carboxylic acid ester and in minor amount the alcohol, water and traces of carboxylic acid.

In the present text, the expression "stream comprising in major amount a given compound" means that the given compound represents at least 85% of the mass of the stream and preferably at least 90% of the mass of the stream.

The expression "stream comprising in minor amount a given compound" means that the given compound represents less than 15% of the mass of the stream and preferably less than 10% of the mass of the stream.

The term "traces" means less than 0.02% by mass and in particular between 0.01% and 0.02% by mass of the compound concerned.

The distillation operation is preferably performed in a distillation column. The feed point where the reaction mixture is introduced is, in general, substantially at the mid-height of the distillation column. It can also be located lower down, at a height between the mid-height of the column and the column still.

The temperature at the distillation still is preferably between 50 and 150° C., preferably between 100 and 130° C.

The defined pressure at the distillation head is preferably between 0.5 and 5 bar absolute; advantageously, the distillation head pressure is between 1 and 2 bar absolute.

According to this first embodiment of the invention in which the esterification reaction is performed in a two-step process, reaction followed by distillation, preferably in an esterification reactor coupled to a distillation column, the iron(III) carboxylate is introduced with the reagents before their introduction into the reactor or alternatively into the reactor before the introduction of the reagents.

In the case of homogeneous catalysis, the liquid acid catalyst enabling homogeneous catalysis is introduced with the reagents before their introduction into the reactor or alternatively into the reactor before the introduction of the reagents. It is possible to purge the reactor one or more times during the reaction in order to free the reaction medium of certain heavy impurities that accumulate in the reactor. In this case, some of the iron(III) carboxylate and of the liquid acid catalyst is removed. In this case, further iron(III) carboxylate and strong protonic acid catalyst may be added, together or separately, continuously or sporadically, into the reactor during the reaction.

In the case of heterogeneous catalysis, the solid acid catalyst is placed in a fixed or fluidized bed in the reactor and the iron(III) carboxylate is introduced into the distillation column during the distillation step. Preferably, the iron(III) carboxylate is introduced into the distillation column still. According to one preferred mode of the invention, the iron(III) carboxylate is not in contact with the solid catalyst enabling heterogeneous catalysis.

According to this first advantageous embodiment of the invention (two-step process), the iron(III) carboxylate is introduced in a concentration ranging from 300 to 1500 ppm and preferably between 400 and 1200 ppm into the reaction medium.

The term "reaction medium" means the medium comprising the carboxylic acid, the alcohol, the carboxylic acid ester and optionally the strong protonic acid catalyst when it is a liquid acid catalyst enabling homogeneous catalysis.

According to the particular embodiment of the invention in which the esterification reaction is performed in the presence of an excess of carboxylic acid, the medium in the distillation still is advantageously withdrawn and recycled by reintroduction upstream of or during the esterification reaction, preferably upstream.

The term "upstream" means that the medium in the distillation still is reintroduced into the mixture of carboxylic acid and alcohol before it has reacted.

In this case, the ratio between the flow rate of the reaction mixture feed (carboxylic acid+alcohol+carboxylic acid ester+optionally the homogeneous catalyst) and the flow rate of the recycled stream is advantageously between 4 and 20 and preferably between 5 and 15.

According to a second embodiment of the invention, the esterification reaction is performed in a one-step process, this step consisting of a reactive distillation operation. The reactive distillation operation takes place, for example, in a reactive distillation column.

According to this particular mode in which the esterification reaction and the distillation are performed in the same step, a vapor stream comprising in major amount the carboxylic acid ester and in minor amount the alcohol, water and traces of carboxylic acid is also obtained at the distillation head.

The definitions of the terms "in major amount", "in minor amount" and traces" are identical to those given previously.

The reactive distillation may be performed under homogeneous or heterogeneous catalysis, preferably under heterogeneous catalysis.

In the case of homogeneous catalysis, the liquid acid catalyst enabling homogeneous catalysis is introduced with the reagents before their introduction into the column or alternatively into the column still before the introduction of the reagents.

In general, the more volatile compound (between the carboxylic acid and the alcohol) is fed into the lower part of the column and the other is fed into the upper part of the column. Generally, it is the alcohol that is the more volatile compound. The alcohol is then preferentially fed into the lower part of the column and the carboxylic acid is preferentially fed into the upper part of the column.

It is most particularly preferred for the carboxylic acid/alcohol mole ratio to be between 1 and 2 and preferably between 1 and 1.5.

The temperature in the reactive distillation still is preferably between 50 and 150° C. and preferably between 90 and 130° C.

According to the invention, the esterification reaction by reactive distillation is preferably performed at a pressure such that the reaction mixture is in liquid form.

The defined pressure at the reactive distillation head is preferably between 0.5 and 5 bar absolute; advantageously, the pressure at the distillation head is between 1 and 2 bar absolute.

For the reactive distillation under homogeneous catalysis, which takes place, for example, in a reactive distillation column, the iron(III) carboxylate is introduced with the reagents before their introduction into the column or alternatively into the column still before or after the introduction of the reagents.

In the case of heterogeneous catalysis, the reactive distillation column especially comprises at least one reaction zone and at least one non-reaction zone.

The packing material that may be used in the reactive distillation column is chosen as a function of the required efficacy. The packing material can be chosen from the packing materials that are well known to those skilled in the art, for instance solids in the form of rings, polylobal extrudates or saddles. Mention may be made, as nonlimiting examples of packing materials, of Raschig rings, Pall rings, Intos rings, Berl saddles, Novalox saddles and Intalox saddles. However, the packing material can also be chosen from structured packings, for example of Flexipac (registered trade name) type, sold by Koch, or Sulzer Chemtech or Sulzer (registered trade names) type, sold by Sulzer.

The reaction zone of the reactive distillation column generally comprises at least one esterification catalytic bed (solid acid catalyst as defined above). The non-reaction zone corresponds to the zone free of catalyst, generally comprising ordered, random or plate packing.

The catalyst can be enclosed in at least one permeable casing, which casing is composed, for example, of a cloth made of fabric, made of synthetic material, for example made of polypropylene, or made of metal fabric.

The catalyst can also be positioned randomly, that is to say freely, inside each catalytic bed of the catalytic zone.

In this case, in order to keep the catalyst in place and to prevent it from being entrained by the liquid stream passing through it, it is generally envisioned for any catalytic bed included in the catalytic zone to rest on any device that allows passage of the liquid but that is impermeable to the catalytic particles, for instance a grille.

When the solid catalyst is positioned randomly, it may be envisioned to use it in the form of a fixed bed, an expanded bed or a fluidized bed. Whether the catalyst is positioned randomly or enclosed in at least one casing, the void fraction which can be conferred on it is generally between 30% and 70%.

In the reactive distillation column, the following steps are generally performed:
1) the alcohol and the carboxylic acid are fed into a distillation column comprising at least one reaction zone and at least one non-reaction zone;
2) the alcohol and the carboxylic acid react in the reaction zone(s) in the presence of a solid catalyst enabling heterogeneous catalysis, and the compounds formed are separated out by distillation.

In general, the more volatile compound (between the carboxylic acid and the alcohol) is fed into the lower part of each reaction zone and the other is fed into the upper part of each reaction zone. Generally, it is the alcohol that is the more volatile compound. The alcohol is then preferentially fed into the lower part of each reaction zone or below each of these zones, and the carboxylic acid is preferentially fed into the upper part of each reaction zone or above each of these zones.

It is very particularly preferable for the reaction in stage 2) to be carried out so that the carboxylic acid/alcohol mole ratio is between 1 and 2, preferably between 1 and 1.5.

The proportion of heterogeneous catalysis solid catalyst in the reactive sections is preferentially between 10% and 50% by volume.

The temperature in the reactive distillation still is preferably between 50 and 150° C. and preferably between 90 and 130° C.

The defined pressure at the reactive distillation head is preferably between 0.5 and 5 bar absolute; advantageously, the pressure at the distillation head is between 1 and 2 bar absolute.

For the heterogeneous catalysis reactive distillation, which takes place, for example, in a reactive distillation column, the iron(III) carboxylate is introduced with the more volatile compound (between the carboxylic acid and the alcohol) which is fed into the lower part of the reaction zone or alternatively into the column still before or after the introduction of the reagents. In the case where there are several reaction zones, the iron(III) carboxylate is introduced below all of the reaction zones or alternatively into the column still before or after the introduction of the reagents. According to one preferred mode of the invention, the iron(III) carboxylate is not in contact with the solid catalyst enabling heterogeneous catalysis.

In this case especially, further iron(III) carboxylate may be added, continuously or sporadically, into the lower part of each reaction zone or alternatively into the column still during the reactive distillation.

According to this second advantageous embodiment of the invention (one-step process), the iron(III) carboxylate is introduced in a concentration ranging from 300 to 1500 ppm and preferably between 400 and 1200 ppm into the reaction medium. The term "reaction medium" means the medium comprising the carboxylic acid, the alcohol, the carboxylic acid ester and optionally the strong protonic acid catalyst when it is a liquid acid catalyst enabling homogeneous catalysis.

According to the invention, the metal surfaces in contact with the esterification medium comprising a carboxylic acid, an alcohol and a strong protonic acid catalyst are surfaces that are capable of withstanding corrosion by the reaction medium.

To this end, materials that withstand corrosion are chosen for the part in contact with the reaction medium, for instance nickel alloys that may contain molybdenum, chromium, cobalt, iron, copper, manganese, titanium, zirconium, aluminum, carbon and tungsten, sold, for example, under the brand name Hastelloy®, mainly Hastelloy C-22 (UNS N06022).

Stainless steels may also be chosen, such as austenitic steels [Robert H. Perry et al., Perry's Chemical Engineers' Handbook, Sixth Edition (1984), pages 23-44] and more particularly stainless steels of 304, 304 L, 316 or 316 L type. A steel with a nickel content of not more than 22% by mass, preferably between 6% and 20% and more preferentially between 8% and 14%, is used.

The steels 304 and 304 L have a nickel content ranging between 8% and 12%, and the steels 316 and 316 L have a nickel content ranging between 10% and 14%.

Use is made more particularly of the 316 L stainless steels.
"Duplex" austeno-ferritic stainless steels of X2CrNiMoN22-5-3 (1.4462) or X2CrNiMoN25-7-4 (1.4410) type according to the European nomenclature may also be chosen.

The following examples illustrate the invention without, however, limiting it.

EXAMPLES

Example 1

P-Toluenesulfonic Acid (PTSA) as Catalyst and Iron III as Corrosion Inhibitor—Effect of the Nature of the Inhibitor and of the Temperature The efficacy of the various corrosion inhibitors will be tested by performing a test that consists, in a closed reactor (stainless steel made of 316L steel with a PTFE (polytetrafluoroethylene) lining), in immersing specimens of stainless steel of 316L type that have been cleaned, dried and weighed beforehand, into a reaction medium derived from an esterification reaction between acetic acid and ethanol in the presence of an acid catalyst enabling homogeneous catalysis, and then in quantifying the rate of corrosion.

These tests were performed according to the standards ASTM G1 "Practice for preparing, cleaning, and evaluating corrosion test specimens" and ASTM G31 "Practice for laboratory immersion corrosion testing of metals".

The reaction medium derived from an esterification reaction between acetic acid and ethanol in the presence of PTSA is reconstituted. The reaction medium has the following composition:
  acetic acid 75.5%;
  ethanol 8%;
  ethyl acetate 9.2%;
  water 6%;
  PTSA 1%;
  sodium bisulfate 0.2%;
  formic acid 0.1%.

The sodium bisulfate is introduced so as to represent the corrosive medium in industrial installations in which the impurities present in the catalyst especially generate sulfate salts, which are highly corrosive toward metals.

Starting with this reaction medium, the various corrosion inhibitors based on iron(III) are tested by adding, according to the tests, an inhibitor chosen from:

iron III nitrate $Fe(NO_3)_3$;
iron III sulfate $Fe(SO_4)_3$, and
iron filings, which, in the presence of acetic acid, generate iron III acetate (the equivalent of 1000 ppm of iron III is added).

The reaction medium is introduced into the reactor and heated to a temperature T of 110° C. or 140° C. depending on the tests. Every 48 hours, the reaction medium is renewed to maintain a constant amount of corrosive agents.

After 350 hours, the specimens are removed, cleaned, dried and weighed. The corrosion rates are then measured for the various tests (with and without each of the inhibitors listed above).

The corrosion rate is calculated as follows:

$$Vc = 8.76 \times 10^4 \cdot \Delta P / A \cdot T \cdot D$$

with
(Vc)=corrosion rate (mm/year);
$\Delta P$=mass variation (g);
A=surface area (cm$^2$);
T=time (hours);
D=density (g/cm$^3$).

The results are collated below in Table 1.

TABLE 1

| | Corrosion rate (mm/year) | | | |
|---|---|---|---|---|
| | Without inhibitor | $Fe(NO_3)_3$ | $Fe(SO_4)_3$ | Fe III Acetate |
| 110° C. | 0.30 | <0.01 | <0.01 | <0.01 |
| 140° C. | 0.40 | <0.01 | 0.30 | <0.01 |

The results show the efficacy of iron III nitrate and acetate, for which the corrosion rate at 140° C. fell from 0.40 mm/year to <0.01 mm/year in the case of iron III nitrate and acetate. The value "<0.01 mm/year" is due to the measuring uncertainty, which does not make it possible to obtain a more precise value of the order of a thousandth.

However, iron III nitrate cannot be used as a corrosion inhibitor in the synthesis of ethyl acetate since it contaminates the ethyl acetate. It is also hazardous to use it since it generates nitrogen oxides (NOx).

In the case of iron III sulfate, which is efficient at 110° C. (corrosion rate less than 0.01 mm/year). However, no further action on the corrosion rate is observed at 140° C., this rate being maintained at 0.30 mm/year with said inhibitor.

Example 2

Comparative Tests Between P-Toluenesulfonic Acid (PTSA) and Methanesulfonic Acid (MSA) with and without Iron III Acetate Corrosion Inhibitor The efficacy of the corrosion inhibitor iron(III) acetate will be tested by performing a test that consists, in a closed reactor (stainless steel made of 316L steel with a PTFE (polytetrafluoroethylene) lining), in immersing specimens of stainless steel of 316L type that have been cleaned, dried and weighed beforehand, into a reaction medium derived from an esterification reaction between acetic acid and ethanol in the presence of various acid catalysts enabling homogeneous catalysis, and then in quantifying the corrosion rate.

The efficacy of the corrosion-inhibiting effect as a function of the catalyst used (PTSA or MSA) is thus compared.

The tests were performed under highly corrosive conditions (140° C.) representative of the conditions experienced during the industrial process for the manufacture of ethyl acetate by esterification in the presence of acetic acid and ethanol. The corrosion rates will be compared according to the acid catalyst used and the presence or absence of the corrosion inhibitor iron(III) acetate, on the main materials used, i.e. austenitic 316L stainless steel and duplex type X2CrNiMoN22-5-3 (1.4462).

The reaction medium derived from an esterification reaction between acetic acid and ethanol in the presence of an acid catalyst is reconstituted.

The reaction medium has the following composition:
acetic acid 75.5%;
ethanol 8.0%;
ethyl acetate 9.7%;
water 6.0%;
formic acid 0.1%;
sodium bisulfate 0.2%;
PTSA 0.5% or MSA 0.28% or MSA 0.8%.

Sodium bisulfate is introduced for the same reasons as those mentioned above in Example 1.

According to the tests, the following catalysts PTSA at 0.5%, MSA at 0.28% or MSA at 0.8% are chosen, and iron (III) acetate is or is not added (depending on the case) as corrosion inhibitor, the iron III acetate being used in a concentration such that it corresponds to 1000 ppm (0.1%) of iron III in the reaction medium.

After placing the reaction medium in the closed reactor (cf. Example 1) containing the cleaned, dried and weighed specimens, it is heated at a temperature of 140° C. for 350 hours with renewal of the reaction medium every 48 hours as in Example 1.

The specimens are then removed from the reactor and are cleaned, dried and weighed.

The corrosion rate calculation is performed by means of the formula given above in Example 1. The results are collated in Table 2 below.

TABLE 2

| MATERIAL | CATALYTIC COMPOSITION (T = 140° C.) | CORROSION RATE (mm/year) |
|---|---|---|
| AISI 316 L | PTSA 0.5% | 0.16 to 0.26 |
| | PTSA 0.5% + Fe(III)OAc 0.1% | <0.01 |
| | MSA 0.28% | 0.23 to 0.33 |
| | MSA 0.28% + Fe(III)OAc 0.1% | <0.01 |
| | MSA 0.80% | 0.98 |
| | MSA 0.80% + Fe(III)OAc 0.1% | <0.01 |
| X2CrNiMoN22-5-3 (1.4462) | PTSA 0.5% | 0.30 |
| | PTSA 0.5% + Fe(III)OAc 0.1% | <0.01 |
| | MSA 0.28% | 0.29 |
| | MSA 0.28% + Fe(III)OAc 0.1% | <0.01 |
| | MSA 0.80% | 1.62 |
| | MSA 0.80% + Fe(III)OAc 0.1% | <0.01 |

The corrosion rate values with 0.5% PTSA and 0.28% MSA in the absence of iron(III) acetate corrosion inhibitor are comparable (about 0.3 mm/year), irrespective of the nature of the material AISI 316L or of X2CrNiMoN22-5-3 (1.4462) type.

It is found that the higher the MSA concentration of the medium (0.8%), the greater the corrosion rate in the absence of iron III acetate.

In particular, in the case of the material of X2CrNiMoN22-5-3 (1.4462) type, when the medium contains MSA at 0.80% and in the absence of the inhibitor iron(III) acetate, the corrosion rate is very high (1.62 mm/year).

On the other hand, as soon as iron(III) acetate is added, the corrosion rate falls to a satisfactory value below 0.01 mm/year.

The invention claimed is:

1. A process for inhibiting corrosion of a metal surface, the process comprising contacting the metal surface with an esterification medium comprising a carboxylic acid, an alcohol, a strong protonic acid catalyst and an iron(III) carboxylate, wherein an esterification between the carboxylic acid and the alcohol occurs in the esterification medium, and wherein the strong protonic acid is an acid with a pKa in water of less than 2.

2. The process as defined in claim 1, wherein the iron(III) carboxylate corresponds to the carboxylic acid in the reaction medium.

3. The process as defined in claim 2, wherein the iron(III) carboxylate is iron(III)acetate.

4. The process as defined in claim 1, wherein the strong protonic acid catalyst is selected from the group consisting of a sulfuric acid, a sulfonic acid, and mixtures thereof.

5. The process as defined in claim 1, wherein the strong protonic acid is a sulfonic acid selected from the group consisting of fluorosulfonic acid, chlorosulfonic acid, trifluoromethanesulfonic acid, methanesulfonic acid, ethanesulfonic acid, camphenesulfonic acid, benzenesulfonic acid, a toluenesulfonic acid, a xylenesulfonic acid and a naphthalenesulfonic acid.

6. The process as defined in claim 1, wherein the strong protonic acid catalyst is introduced at a concentration of from 0.1% to 15% by mass, relative to the reaction medium.

7. The process as defined in claim 6, wherein the strong protonic acid catalyst is introduced at a concentration of from 0.2% to 10% by mass.

8. The process as defined in claim 6, wherein the strong protonic acid catalyst is introduced at a concentration of from 0.3% to 2% by mass.

9. The process as defined in claim 1, wherein the iron(III) carboxylate is introduced in a concentration ranging from 300 ppm to 1500 ppm into the reaction medium.

10. The process as defined in claim 9, wherein the iron(III) carboxylate is introduced in a concentration ranging from 400 ppm to 1,200 ppm.

11. The process as defined in claim 1, wherein the carboxylic acid is an aliphatic carboxylic acid containing from 1 to 6 carbon atoms.

12. The process as defined in claim 11, wherein the carboxylic acid is acetic acid.

13. The process as defined in claim 1, wherein the alcohol is selected from the group consisting of ethanol, n-propanol, butanol and cyclohexanol.

14. The process as defined in claim 13, wherein the alcohol is ethanol.

15. The process as defined in claim 1, wherein the metal surface is a surface that can withstand corrosion by the reaction medium, and is comprised of a nickel alloy that comprises a metal selected from the group consisting of molybdenum, chromium, cobalt, iron, copper, manganese, titanium, zirconium, aluminum, carbon and tungsten.

16. The process as defined in claim 15, wherein the esterification reaction is performed in a one-step process and comprises a reactive distillation operation.

17. The process as defined in claim 15, wherein the metal surface is comprised of an austenitic or austeno-ferritic stainless steel.

18. The process as defined in claim 1, wherein the esterification reaction is performed in a two-step process in which the esterification reaction is followed by a distillation operation.

19. The process as defined in claim 18, wherein the esterification reaction is performed at a temperature of 50° C. to 150° C. and at a pressure of from 0.5 bar to 5 bar absolute.

20. The process as defined in claim 19, wherein the temperature is from 100° C., to 130° C.

* * * * *